US00PP30541P3

(12) United States Plant Patent
Bourne

(10) Patent No.: US PP30,541 P3
(45) Date of Patent: May 28, 2019

(54) GRAPEVINE NAMED 'SV28-100-849'

(50) Latin Name: *Vitis vinifera*
Varietal Denomination: SV28-100-849

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 15/998,175

(22) Filed: Jul. 11, 2018

(65) Prior Publication Data

US 2019/0029155 P1 Jan. 24, 2019

Related U.S. Application Data

(60) Provisional application No. 62/604,734, filed on Jul. 18, 2017.

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./156, 205
See application file for complete search history.

*Primary Examiner* — Susan McCormick Ewoldt
*Assistant Examiner* — Karen M Redden
(74) *Attorney, Agent, or Firm* — Baker Manock & Jensen, PC; Eric C. Cole

(57) ABSTRACT

A new and distinct variety of grapevine plant named 'SV28-100-849' particularly characterized by its ellipsoidal shaped, red skinned berries which are large, sweet and have very firm texture. Additionally, flower clusters and berries are very responsive to exogenous gibberellic acid application. When applied at full flowering, gibberellic acid reduces fruit set, producing loose, well-filled clusters. Gibberellic acid applied to clusters after berry set increases the berry size considerably, in some cases approximately doubling berry size over when combined with trunk girdling.

2 Drawing Sheets

Latin name of the genus and species of the plant claimed: The plant claimed relates to a new and distinct variety of *Vitis vinifera*.

Variety denomination: The plant claimed shall be known as 'SV28-100-849'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV28-100-849'. As used herein, 'grapevine' refers to all plant parts including, vines, canes, tendrils, leaves, fruit and roots of 'SV28-100-849'. Grapevine named 'SV28-100-849' is the result of an effort to produce an early ripening, red, seedless table grape with fruit characteristics superior to currently available red skinned grape cultivar 'Flame Seedless' (unpatented). This new cultivar originated from a cross conducted in May 2007 near McFarland, Calif. between pistillate grapevine plant selection 'SV18-9-1' (unpatented) and pollen parent 'Princess' (unpatented). Resultant ovules from the cross were harvested 42 days after pollination and cultured on 'McCown's Woody Plant Medium' at a temperature of 22° C. for twelve weeks. Subsequently, the resultant embryonic plants were cultured in the same medium in the laboratory under twelve hours of light from standard fluorescent lamps at 26.4° C. The seedlings from this effort were transplanted to the greenhouse in October of 2007 and grown in the greenhouse at 26.4° C. with 12 hours' illumination under high pressure sodium vapor lamps. The seedling population of 960 plants was planted in the field in the spring of 2008 near Delano, Calif. The new grapevine was selected from this seedling population on Jul. 13, 2010. It was then propagated by cuttings and bench grafted to 'Freedom' (unpatented) rootstock in 2011. The present invention has been found to retain its distinctive characteristics through two successive asexual propagations.

Grapevine named 'SV28-100-849' differs from the female parent grapevine 'SV18-9-1' (unpatented) in that grapevine named 'SV28-100-849' has ellipsoidal shaped, red skinned, seedless berries and flowers with functional pollen, whereas the female parent grapevine 'SV18-9-1' (unpatented) has spherical shaped, red skinned berries with partially lignified seed traces and flowers that are pistillate.

Grapevine named 'SV28-100-849' differs from its male parent 'Princess' (unpatented) in that grapevine named 'SV28-100-849' has red skinned berries which keep very well for extended periods in cold storage, whereas the male parent 'Princess' (unpatented) has oblong shaped, yellow berries that brown internally while in cold storage.

Grapevine named 'SV28-100-849' differs from the commercial cultivar 'Flame Seedless' (unpatented) in that grapevine named 'SV28-100-849' has ellipsoidal shaped, red skinned berries which do not require exogenous ethephon application to achieve full color in the southern San Joaquin Valley. Commercial cultivar 'Flame Seedless' (unpatented) has spherical shaped red skinned berries which do require application of ethephon to achieve full color in the southern San Joaquin Valley. The berries of grapevine named 'SV28-100-849' have a superior eating quality and larger berries at harvest after standard vineyard practices of application of exogenous gibberellic acid and girdling of the vine trunks as compared to commercial cultivar 'Flame Seedless' (unpatented). Additionally, grapevine named 'SV28-100-849' has well-sealed berries tips with no tendency to crack whereas commercial cultivar 'Flame Seedless' (unpatented) has a pronounced stigmatic scar causing berry splitting in some years.

Grapevine named 'SV28-100-849' is most similar to Sheegene-12 (U.S. Plant Pat. No. 20,252) which ripens about the same time as the extant cultivar. Grapevine named 'SV-100-849' may be distinguished from 'Sheegene-12' (U.S. Plant Pat. No. 20,252) by its greater fruitfulness, generally two clusters per shoot versus 1 cluster per shoot for 'Sheegene-12' (U.S. Plant Pat. No. 20,252) and by its slightly darker red fruit color.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. Red skinned;
2. Very firm berry texture; and
3. Very large, ellipsoidal shaped berries with sweet taste.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken in 2016 from a plant about 5 years-old, grown in a field near McFarland, Calif.

DETAILED BOTANICAL DESCRIPTION

Figure 1:
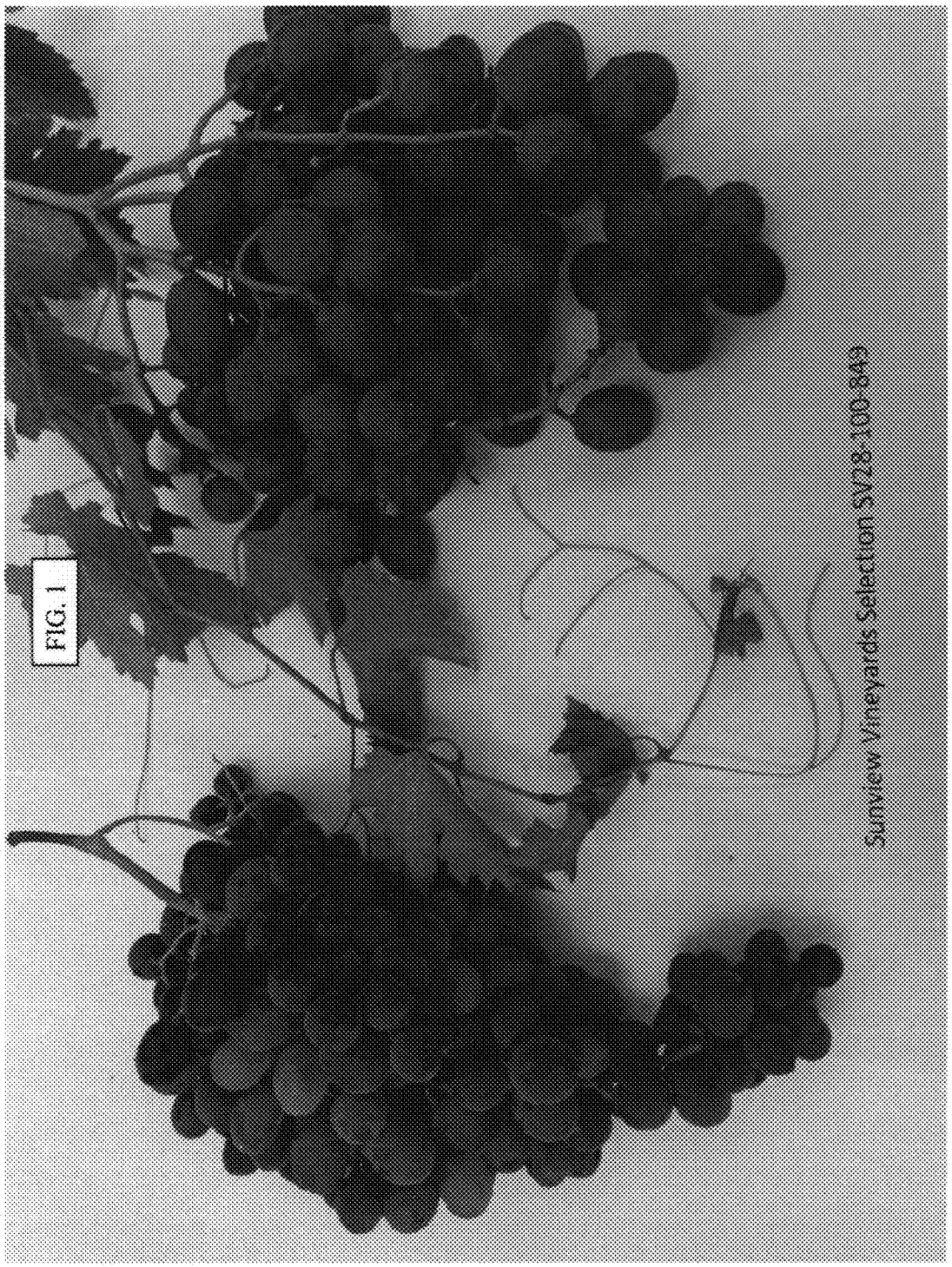
FIG. 1 Natural fruit cluster and cluster sprayed with gibberellic acid with shoots, leaves, tendrils and shoot tips.
Figure 2:
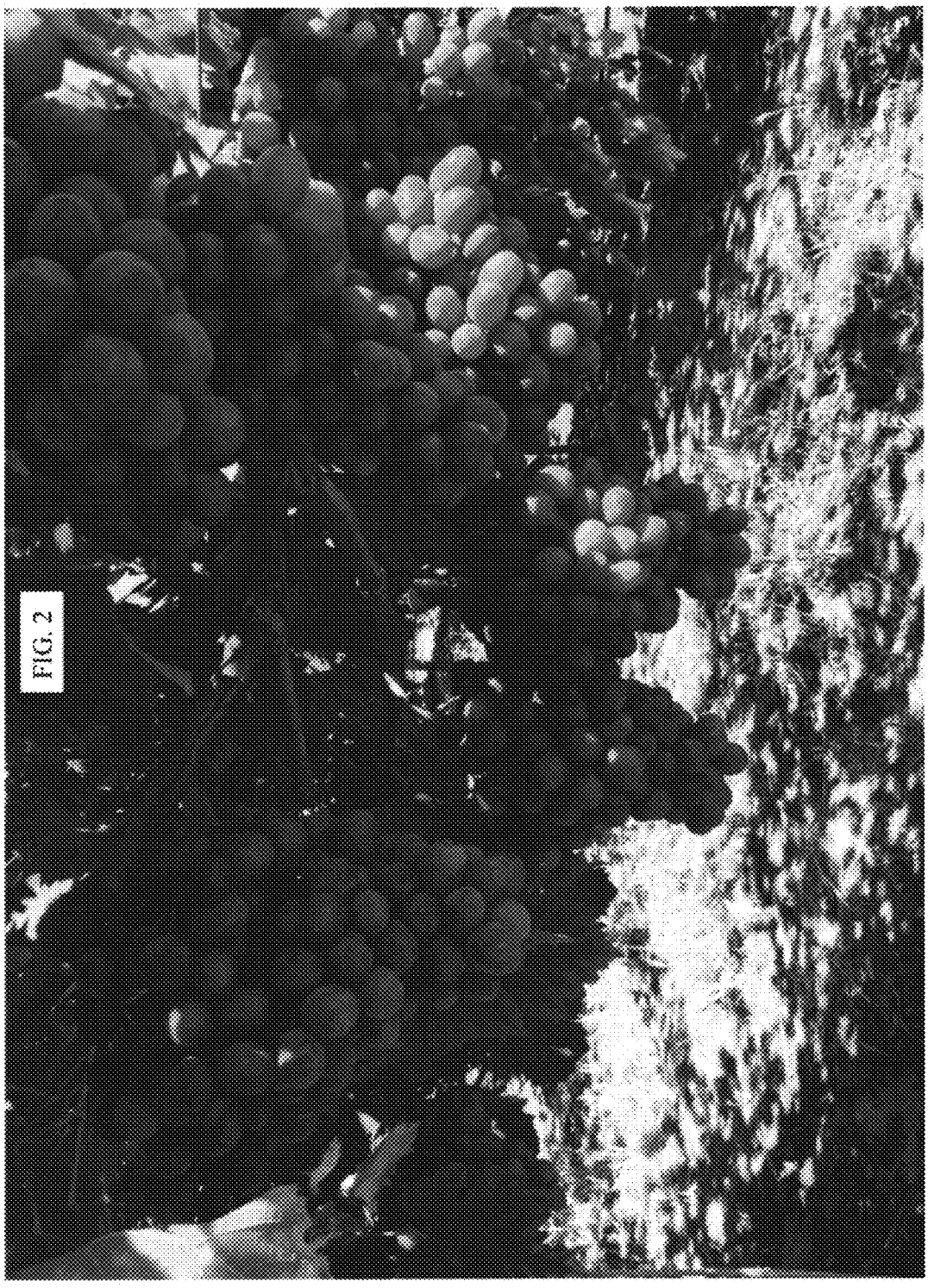
FIG. 2 Fruit clusters on vine sprayed with gibberellic acid and trunk girdled.

The following detailed description sets forth the distinctive characteristics of 'SV28-100-849'. Descriptions of the new invention apply to vines of 'SV28-100-849' grown on 'Freedom' rootstock at a density of 1,537 vines per hectare grown near McFarland, Calif. in 2017. These vines were in their sixth year of full production, having been planted in 2011. These descriptions are believed to apply generally to the new variety grown under similar circumstances elsewhere. References to color correspond to The Royal Horticultural Society's Colour Chart (2001), The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in *Descriptors for Grapevine* (*Vitis* spp.) (Anonymous, International Plant Genetic Resources Institute, 1997, ISBN 92-9043-352-3).

Classification:

*Family.*—Vitaceae.

*Botanical name.*—*Vitis vinifera.*

*Variety name.*—'SV28-100-849'.

Plant:

*Vigor.*—Medium; vines spur-pruned and shoot thinned to 32 shoots.

*Density of foliage.*—Moderate.

*Productivity.*—Very productive when spur pruned, up to 32,000 kg/hectare.

*Hardiness.*—Hardiness observed to 0° C.

*Rootstock.*—'Freedom' (unpatented).

Trunk:

*Shape.*—Broadly elliptical.

*Straps.*—Long, split.

*Surface texture.*—Shaggy.

*Trunk circumference.*—17.9 cm at 1.0 m of height.

*Inner bark color.*—RHS 174A Greyed orange group 167C.

*Outer bark color.*—RHS Greyed orange group 166B.

Mature leaves:

*Average blade length.*—14.5 cm.

*Average blade width.*—17.5 cm.

*Size of blade.*—Large.

*Shape.*—Pentagonal.

*Anthocyanin coloration of main veins on the upper side of the blade.*—Absent.

*Mature leaf profile.*—Cupped upwards around entire margin.

*Blistering* (*upper surface*).—Absent.

*Leaf blade tip.*—Curved upward.

*Margins.*—Lobed, serrated, undulating.

*Apex.*—Narrowly acute.

*Bases.*—Sagittate.

*Thickness.*—Medium.

*Undulation of blade between main and lateral veins.*—Slight.

*Shape of teeth.*—Broadly conical, both sides convex.

*Length of teeth.*—4-9 mm.

*Ratio length/width of teeth.*—About 1:1.

*General shape of petiole sinus.*—Variable; open (conical) to closed.

*Tooth at petiole sinus.*—Absent.

*Petiole sinus limited by veins.*—Absent.

*Shape of upper lateral sinus.*—Closed.

*Prostrate hairs between veins* (*lower surface*).—Absent.

*Erect hairs between veins* (*lower surface*).—Absent.

*Prostrate hairs on main veins* (*lower surface*).—Absent.

*Density of erect hairs on main veins* (*lower surface*).—Moderately abundant for most of the length of the main vine. Dense at the junction of the main vein and large veins.

*Prostrate hairs on main veins* (*upper surface*).—Moderately abundant at the junction of the main vein and lateral veins.

*Upper surface.*—Summer color: RHS Green Group 137A. Surface texture: Smooth. Surface appearance: Dull. Goffering of blade: Absent.

*Lower surface.*—Summer color: RHS Green Group 141C. Anthocyanin coloration of main veins on lower leaf surface: Absent. Anthocyanin coloration on laterals: No. Glossiness: Low. Pubescence: Absent. Surface texture: Rough. Surface appearance: Dull.

*Petiole.*—Length: 12.7 cm. Length of petiole compared to middle vein: Slightly shorter. Density of prostrate hairs: Absent. Density of erect hairs: Absent. Shape of base of petiole sinus: Mostly open; outline is ovate. Color: RHS Green Group 143C, with red streaks, Red-Purple Group N66C.

Tendrils:

*Number.*—Bifurcated and trifurcated; forming mostly at alternate nodes above node 7.

*Length.*—28.2 cm.

*Diameter.*—4.6 mm.

*Texture.*—Smooth.

*Color.*—In shade: RHS Yellow Green Group 145A. In sun: RHS Yellow Green Group 144B.

Growing tips (young shoot):

*Pubescence.*—Abundant, prostrate.

*Color.*—RHS Yellow Green Group 144C.

*Anthocyanins.*—Absent.

*Shape.*—Flattened.

*Apex.*—Open.

*Shoot attitude.*—Semi-erect.

Flowers:

*Flower sex.*—Perfect.

*Position of first flowering nodes.*—Usually on nodes 4 or 5.

*Number of inflorescences per shoot.*—Generally two per shoot on nodes 4 and 5 or on nodes 5 and 6.

*Flower cluster length including peduncle.*—About 28 cm.

*Peduncle color.*—Yellow green group 145A with occasional red streaking: red purple group 60A.

*Flower cluster conformation.*—Cylindrical with top shoulder about 11.5 cm.

*Calyptra color.*—RHS 141C (green group).

*Ovary length.*—1.5 mm.

*Ovary width.*—1.0 mm.

*Ovary color.*—RHS Yellow green group 144C.

*Filament length.*—2.0 mm.

*Filament color.*—Translucent, absence of pigmentation.

*Anther length.*—1.0 mm.

*Anther color.*—RHS Yellow Group 8B.

*Date of full bloom.*—May 4th.

Fruit:

*Ripening period.*—Early mid-season, about 12 days after 'Flame Seedless' at Delano, Calif.

*Date of ripening.*—July 25$^{th}$ at McFarland, Calif.

*Use.*—Fresh market.

*Keeping quality.*—Very good, fruit has stored up to 8 months with no decay.

*Shipping quality.*—Good.

*Date of first harvest.*—*July* 25th.

*Solids-sugar.*—High, about 20 brix at full maturity.

*Refractometer test.*—20.0 brix.

*Bunch.*—Size: Medium. Length (peduncle excluded): About 31.4 cm. Width: About 15.0 cm. Weight: Natural, without gibberellic acid treatment: 469.0 g. With gibberellic acid treatment: 448.0 g. Density: Well-filled, but loose. Number of berries: 136. Form: Conical.

*Peduncle.*—Length: About 6.7 cm. Lignification: Medium. Color: RHS Yellow Green Group 144C.

*Berry.*—Size: Large. Uniformity of size: Uniform. Weight. Natural, without gibberellic acid treatment: About 3.5 g. With gibberellic acid treatment: About 4.8 g. Shape: Natural, without gibberellic acid treatment: Ellipsoidal. With gibberellic acid treatment: Ellipsoidal. Presence of seeds: Seedless; most berries develop one or two small, soft rudimentary seeds less than 1.0 mm in length. Cross section: Circular. Dimensions: Longitudinal axis: About 2.1 cm at base. Horizontal axis: About 1.7 cm. Skin color (without bloom): RHS Red Purple Group 61B. Juiciness of flesh: Very juicy. Berry firmness: Very firm. Particular flavor: Neutral, typical *vinifera*. Bloom (cuticular wax): Heavy. Pedicel length: 0.9 cm. Berry separation from pedicel: Moderately easy.

*Skin.*—Thickness: Medium. Texture: Tender. Reticulation: Absent. Roughness: Absent. Tenacity: Tenacious to flesh. Tendency to crack: Resistant.

Disease and insect resistance: Moderately susceptible to powdery mildew which may be controlled with standard fungicides in California.

Having thus described and illustrated my new variety of grapevine, I claim:

1. A new and distinct variety of grapevine plant named 'SV28-100-849', and parts thereof, substantially as illustrated and described herein.

* * * * *